United States Patent [19]

Gatos et al.

[11] 4,011,745
[45] Mar. 15, 1977

[54] SEMICONDUCTOR SENSORS

[75] Inventors: Harry C. Gatos, Weston, Mass.;
Jacek Lagowski, Warsaw, Poland

[73] Assignee: Massachusetts Institute of Technology, Cambridge, Mass.

[22] Filed: Nov. 7, 1975

[21] Appl. No.: 629,839

Related U.S. Application Data

[60] Continuation of Ser. No. 492,118, July 26, 1974, abandoned, which is a division of Ser. No. 290,666, Sept. 21, 1972, Pat. No. 3,887,937.

[52] U.S. Cl. .................................................. 73/23
[51] Int. Cl.² ...................................... G01N 23/00
[58] Field of Search ...................... 73/23; 307/308

[56] References Cited

UNITED STATES PATENTS

| | | | |
|---|---|---|---|
| 2,965,842 | 12/1960 | Jacobson | 73/23 X |
| 3,194,053 | 7/1965 | Shang | 73/23 |

OTHER PUBLICATIONS

Lagowski et al., "Electronic Characteristics of Real CdS Surfaces", Surface Science 29 (1972), pp. 213-229.

*Primary Examiner*—Charles A. Ruehl
*Attorney, Agent, or Firm*—Arthur A. Smith, Jr.; Robert Shaw; Martin M. Santa

[57] ABSTRACT

A semiconductor sensor adapted to detect with a high degree of sensitivity small magnitudes of a mechanical force, presence of traces of a gas or light. The sensor includes a high energy gap (i.e., ~ 1.0 electron volts) semiconductor wafer. Mechanical force is measured by employing a non-centrosymmetric material for the semiconductor. Distortion of the semiconductor by the force creates a contact potential difference (cpd) at the semiconductor surface, and this cpd is determined to give a measure of the force. When such a semiconductor is subjected to illumination with an energy less than the energy gap of the semiconductors, such illumination also creates a cpd at the surface. Detection of this cpd is employed to sense the illumination itself or, in a variation of the system, to detect a gas. When either a gas or light is to be detected and a crystal of a non-centrosymmetric material is employed, the presence of gas or light, in appropriate circumstances, results in a strain within the crystal which distorts the same and the distortion provides a mechanism for qualitative and quantitative evaluation of the gas or the light, as the case may be.

11 Claims, 8 Drawing Figures

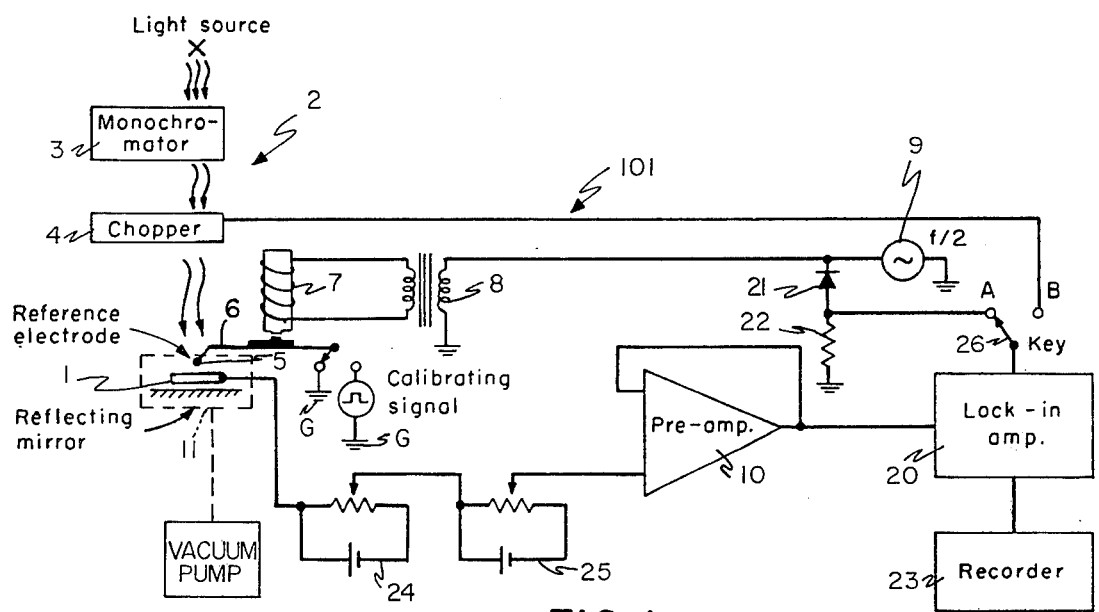
FIG. 1
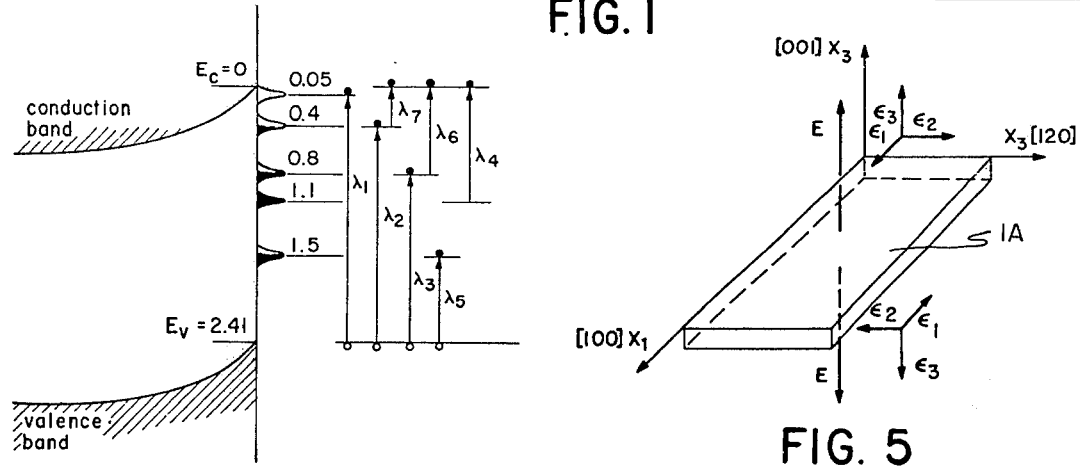
FIG. 2
FIG. 5
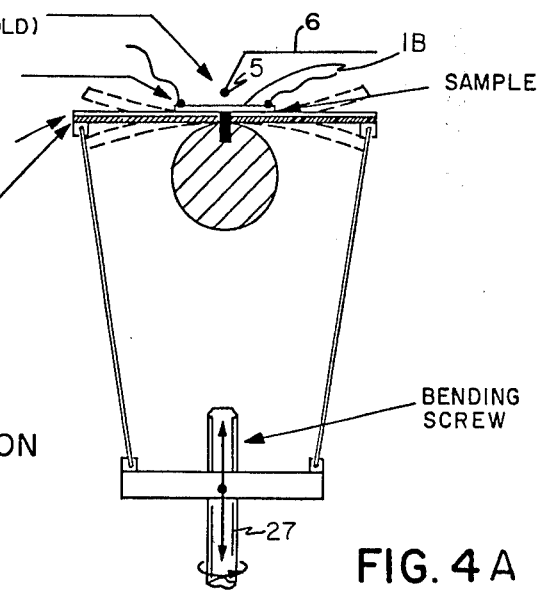
FIG. 4C
FIG. 4A

SEMICONDUCTOR SENSORS

The invention described herein was made in the performance of work under a NASA contract and is subject to the provisions of Section 305 of the National Aeronautics and Space Act of 1958, Public Law 85-568 (72 Stat. 435; 42 U.S.C. 2457).

This is a continuation of application Ser. No. 492,118, filed July 26, 1974 (now abandoned), which was a division of application Ser. No. 290,666, filed Sept. 21, 1972 (now U.S. Pat. No. 3,887,937, granted June 9, 1975).

The present invention relates to sensors and, in particular, to semiconductor sensors that are useful to detect very small values of mechanical force, traces of a gas or light.

Of interest in connection with the invention are the following journal articles as well as the reference cited in said articles: "Determination of Surface State Energy Positions by Surface Photovoltage Spectrometry: CdS," Surface Science, 26, (1971), pp. 317–320, Balestra et al.; "Photovoltage Inversion Effect and Its Application to Semiconductor Surface Studies: CdS", Surface Science, 27, (1971), pp. 547–558, Lagowski et al.; "Determination of Surface State Parameters From Surface Photovoltage Transients: CdS", Surface Science, 29, (1971), pp. 203–212, Lagowski et al.; "Photomechanical Effect in Noncentrosymmetric Semiconductors—CdS", Appl. Phys. Lett., Vol. 20, 1, 1 Jan. 1972, pp. 14–16, Lagowski et al.; "Photovoltage Inversion Effect Resulting From a Continuous Spectrum of Surface States: Surface Science, 30, (1972), pp. 653–658, Lagowski et al.; "Electronic Characteristics of 'Real' CdS Surfaces", Surface Science, 29, (1972), pp. 213–229, Lagowski et al.; "Surface Piezoelectric Effect in Non-Centrosymmetric Semiconductors: CdS", Surface Science, 30, (1972), pp. 491–496, Lagowski et al.; and "Surface Photovoltage Spectroscopy—A New Approach to the Study of High-Gap Semiconductor Surfaces," Gatos et al.

Surface photovoltage spectroscopy, which is in the term used by the present inventors to described their method of studying electron configurations on semiconductor surfaces, is based on the photostimulated de-population and population of surface states brought about by sub-bandgap (i.e., an energy less than the energy gap of the semiconductors) monochromatic illumination, while the overall number of bulk free carriers remains essentially unchanged. Such transitions and their transients (as determined by changes in the contact potential difference) allow the direct determination of the energy positions and the dynamic parameters of the surface states. Surface photovoltage spectroscopy has been successfully applied by the present inventors to the surfaces of CdS, ZnO and GaAs, high energy gap semiconductors.

The photovoltaic effect, i.e., the appearance of a voltage upon illuminating a semiconductor-metal rectifier, was reported nearly one hundred years ago. However, it was not until 1948 that this effect was employed to study semiconductor surfaces, primarily through band-to-band transitions leading to the generation of free carriers. In this type of experiment, the role of surface states was studied through the trapping and recombination of excess carriers. The present inventors have observed surface photovoltage in the above materials under sub-bandgap illumination, where apparently no band-to-band transitions are involved. Under such sub-bandgap illumination, the surface photovoltage is associated with discrete electron transitions from the surface states into the conduction band and from the valence band into the surface states.

In the case of non-centrosymmetric (piezoelectric) high energy gap semiconductor compounds, a stress applied through mechanical bending of thin wafers corresponds to an applied electric field which causes an increase or decrease in the surface barrier height depending on the direction of bending (surface piezoelectric effect). In the latter case it has been shown that equilibrium is established between the surface states and the bulk. Thus, it is now possible, by combining controlled mechanical bending (and unbending) and surface photovoltage spectroscopy, to study the characteristics of the surface states under equilibrium conditions. It is also possible to relate the surface states to the magnitude of the mechanical bending force, thereby to supply a mechanism for determining that force. Accordingly, a principal object of the present invention is to provide a semiconductor device suitable for use as a mechanical force sensor.

When the semiconductor is placed in a vacuum and traces of a gas are introduced into the system, the condition of the surface states is modified and the gas can be sensed thereby. A further object, therefore, is to provide a semiconductor gas sensor.

The high energy gap semiconductor if subjected to light exhibits a contact potential difference which is a function of the amount of radiation and the frequency thereof. Furthermore, if the semiconductor is non-centrosymmetric, it undergoes strain, that is, elastic deformation or mechanical vibrations. Either phenomenon can be noted. It is another object, therefore, to provide a sensing system to detect the presence of light and to indicate the frequency of the light.

These and other objects are found in the description that follows and are particularly pointed out in the appended claims.

The objects of the invention are embodied in a sensing system that includes a high energy-gap semiconductor wafer. Means is provided to effect changes of population of the surface states of the semiconductor thereby to effect changes in the surface barrier without affecting the bulk carrier concentration in the bulk material. There is also provided means for detecting the changes in the surface states as a consequence of said changes in population and for relating the same to the thing to-be-sensed.

The invention will now be discussed with reference to the accompanying drawing in which:

FIG. 1 is a schematic of a semiconductor sensing system of the present invention, partially block diagram in form;

FIG. 2 is a schematic representation of the surface states of the prismatic surfaces of a CdS semiconductor and the associated electron transitions;

Figure 4B:
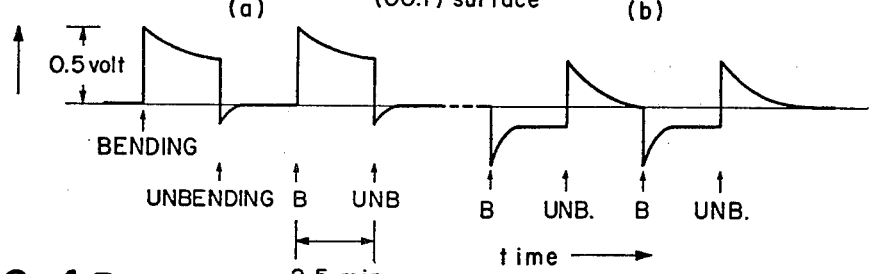
FIG. 4B is a graph of contact potential difference as a function of bending and unbending of the crystal shown in FIG. 4A.
Figure 4D:
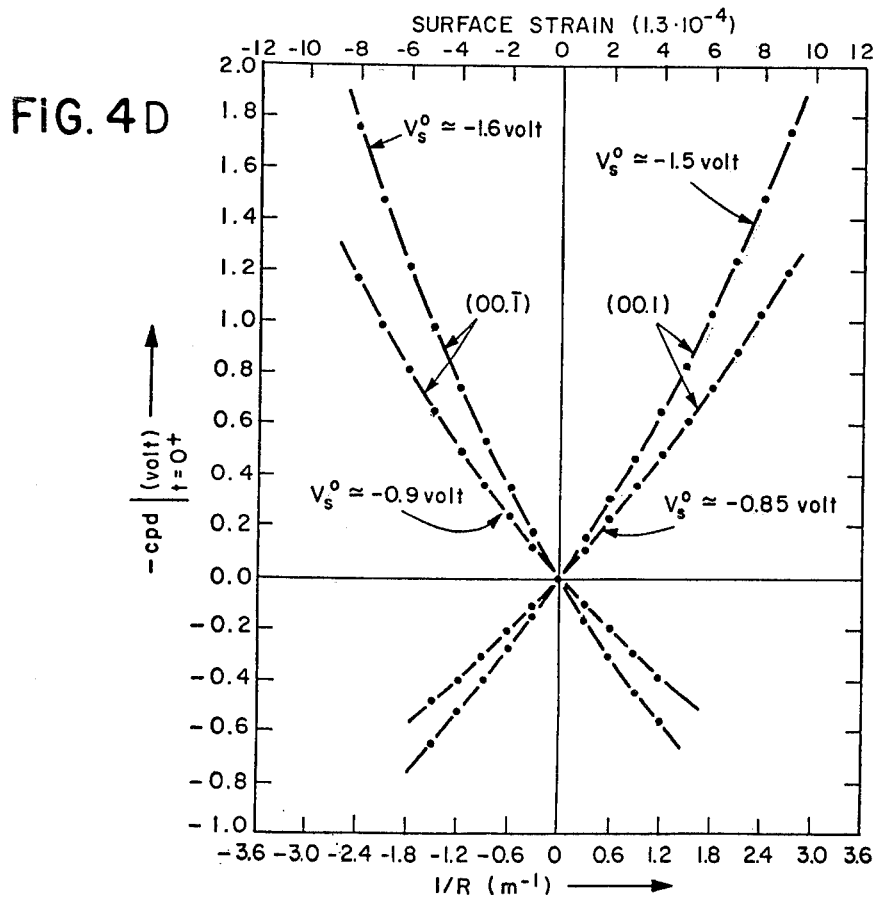
FIG. 4A is a schematic representation of a part of a system that is a modification of the system of FIG. 1 and is intended to relate bending of a non-centrosymmetric crystal and contact potential difference (cpd)
FIG. 4C shows orientation of the crystal of FIG. 4A.

FIG. 4D relates changes in cpd to the radius of bending and surface strain; and

Figure 3:
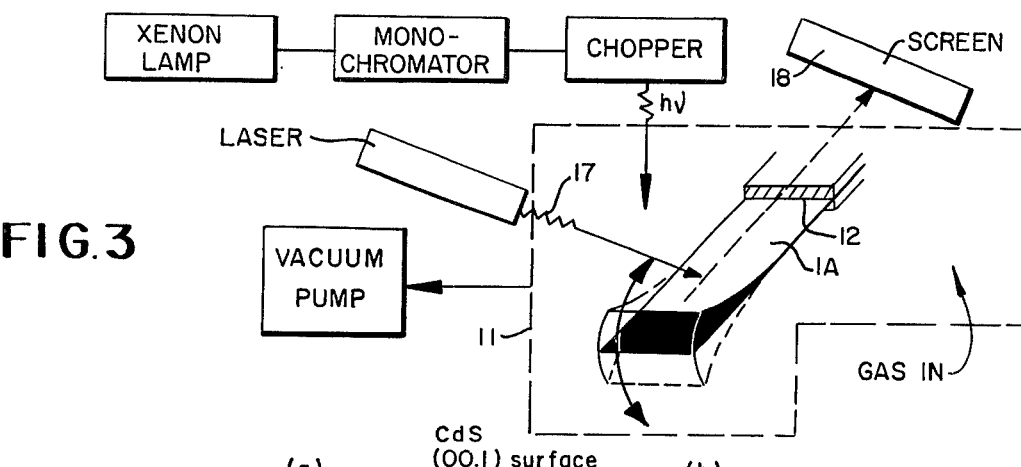
FIG. 3 shows a part of a system which is a modification of the system of FIG. 1 and shows a CdS wafer secured at one end thereof and subjected to deformation by changes effected in the surface states of the crystal.

FIG. 5 illustrates the crystallographic orientation of the semiconductor wafer of FIGS. 3 and 4.

Turning now to the drawing a sensor or sensing system of the present invention is shown at 101. The system 101 comprises a high energy-gap semiconductor wafer 1 which may be made, for example, of CdS, ZnO or GaAs. As used herein "high" denotes a semiconductor having a gap~1.0 ev or higher at room temperature; operation at lower than room temperatures allows use of proportionately lower energy-gap materials. Such other materials can be employed within the present teachings and the gap thereof is considered "high" in the context of this specification. The sensing system 101 can be employed to measure an occurrence which effects changes in the population of the surface states of the semiconductor wafer, to effect changes in the surface barrier but without appreciably affecting the electrical carrier concentration in the bulk material thereof. Such an occurrence can be a force resulting in a bending moment upon the wafer 1, which results in a contact potential difference (cpd) at the wafer surface; or the occurrence can be the presence of the photons again resulting in a cpd; or the occurrence can be the presence of a gas in a vacuum environment which results in changes in cpd otherwise effected — all as discussed in detail hereinafter. Thus, all these phenomena can be detected by voltage sensing means, but, as is explained in later paragraphs, the latter two can be sensed by noting deformation of the wafer due to the said population changes.

The cpd is measured by voltage sensing means which, includes essentially most of the circuit elements in FIG. 1, as now explained. (The explanation given here is taken to a large measure from the article entitled, "Electronic Characteristics of 'Real' CdS Surfaces", which can be referred to for amplification of the present disclosure.) The voltage sensing circuitry includes a gold-base reference electrode or probe 5 driven by a vibrating reed 6 to which the electrode is spot welded. In test apparatus employing the elements shown in FIG. 1, the reed 6 was vibrated at a frequency of the order of 100 cycles/sec. which was twice the driving signal frequency, thus preventing inductive pick-up of this signal by the narrow bandwidth lock-in amplifier labeled 20. However, the vibrator current lead wires carried more than one ampere, and the second harmonic portion of the signal could spuriously contribute to the cpd signal unless care were taken in the positioning of signal leads. Thus, it was found that a parallel arrangement of the lead wires could result in a cpd error as large as 0.05 V. The probe 5 was grounded, as shown, so that cpd signals generated with respect to the other materials were dissipated as ground loop currents. Probe and wafer leads were of the same 30-gauge copper wire to minimize the spurious effect of series thermal emf's. The distance between the semiconductor wafer 1 and the reference electrode 5 was about 0.1 mm.

Vibration of the reed 6 is, in the system of FIG. 1, effected by a solenoid 7 which is fed by a transformer 8. The transformer 8, in turn, receives power from a supply 9, a portion of whose output is rectified by a diode 21 acting with a current limiting resistor 22. The surface photovoltage is measured as a change in the steady state cpd with respect to the reference electrode 5 by means of an off-null-measurement arrangement, as now explained. The effect of periodically changing the position between the electrode 5 and the surface of the semiconducting wafer 1 is to create an a-c displacement signal, at the frequency of supply 9, which is applied across a pre-amplifier 10, the output of which is connected as one input to the lock-in amplifier 20. When switch 26 is in position A, a reference a-c signal at the frequency of supply 9 is supplied as the other input to lock-in amplifier 20 with the result that the output of this amplifier is representative of the periodic changes in cpd arising from the interaction of vibrating electrode 5 with crystal 1, such changes being recorded at 23 to provide a reference that can be compared when the crystal is excited by a chopped light source alone. A pair of R-C circuits 24 and 25 serves to reduce the magnitude of spurious signals. It should be noted that the distance between the wafer and the electrode should be small enough to ensure a measurable signal for a suitably small vibrational amplitude and to render negligible other signals which may be generated with respect to any material electronically coupled to the system 101. However, this distance must not be so small as to lead to electrostatic attraction and, thus, affect the linearity of the a-c signal as a function of cpd. When the switch 26 is connected to its terminal B and the electrode 5 is stationary, that is, non-oscillatory, the equivalent of the oscillatory situation can be achieved by rendering periodic changes upon the cpd. This can be accomplished by creating the cpd in the first instance by radiation from a light source through a monochromator 3, and introducing periodicity by a chopper 4. The resultant a-c displacement signal at the frequency of chopper 4 is applied to pre-amplifier 10, the output of which is connected as one input to amplifier 20. By reason of switch 26 being in position B, the other input to amplifier 20 is a reference a-c signal at the frequency of chopper 4, so that the output of amplifier 20 is representative of the periodic changes in cpd arising from the interaction of the chopped light with the crystal, as later discussed. First, however, there follows in the next few paragraphs, a discussion of the force sensor system.

Elsewhere herein it is mentioned that changes in the population of the surface states can be effected by illuminating the semiconductor crystal but that, in the case of non-centrosymmetric crystals, that same change can be effected by application of a mechanical bending force upon the crystal. The latter effect is now discussed with reference to FIG. 4A wherein the semiconductor crystal is designated 1B. A sensing circuit like the circuit in FIG. 1 can be employed. In work done, a surface piezoelectric effect was found whereby mechanical bending of CdS wafers with an (00.1) orientation caused pronounced changes (of the order of one volt) in the contact potential difference. This effect was attributed to the polarization induced in the depletion layer by the mechanical stress. The wafer 1B employed measured 13 × 3 × 0.08 mm. It was cut from a high purity, n-type single crystal with a resistivity of about 2 ohm-cm, mechanically ground, polished with an 0.25 μm particle size abrasive. It was chemically etched (in 0.5 N $k_2Cr_2O_7$:16 N $H_2SO_4$) to the final dimensions to remove all surface damage introduced during polishing. Ohmic contacts were made employing indium in a hydrogen atmosphere. Contact potential difference (cpd) was measured by use of the vibrating gold-reference electrode 5 with an accuracy of better than 1 mV employing an off-null-measurement arrangement. The wafer was bent parallel to the [210] or [010] direction with the apparatus shown schematically in FIG. 4A. The desired radius of curvature (in the range of −20 to +20 cm) was conveniently obtained by means of calibrated bending screw 27. During bending the distance between the central part of the wafer and the reference electrodes remained constant. The strain induced by bending was measured with strain gauges attached to the wafer surface.

Typical cpd transients resulting from bending and unbending of a (00.1) wafer are shown in FIG. 4B. They are analogous to field effect transients. They were perfectly reproducible and reversible after the initial bending-unbending cycle, which is not shown here. During the initial bending the decrease in the surface barrier (increase in cpd) stimulates filling of the surface states since their occupation is below the equilibrium value. Upon unbending this increased (equilibrium) occupation of the surface states is clearly manifested as a decrease in the steady state cpd (an increase in the surface barrier). No further change in the steady state occupation of the surface states (in the unbent condition) takes place in subsequent bending-unbending cycles. Accordingly, the present results represent the cpd transients after the initial bending-unbending cycle. The cpd transients of FIG. 4B correspond to stress-induced discharging and charging of the surface states.

The dependence of the cpd on the radius of bending and on the induced strain at the surface are shown in FIG. 4D for the (00.1), Cd, and (00.$\bar{1}$), sulfur, surfaces at two steady state values of the surface barrier height labeled $V_s^0$. It is seen that bending induces a polarization (a change in surface barrier height) which is of opposite sign in the two types of surfaces. This result confirms the peizoelectric nature of the present effect. The two steady state values of $V_s^0$ shown in FIG. 4D correspond to two different ambients: room atmosphere (higher value of $|V_s^0|$) and vacuum of about $10^{-4}$ torr (lower value of $|V_s^0|$). The sensitivity of the present effect on the surface barrier height indicates that it is primarily a surface effect with no appreciable contributions from stress-induced bulk effects. Consistent with this conclusion, it was found that the magnitude of the effect decreased by lowering the surface barrier height with white light illumination; in fact the effect could no longer be observed when a flat band condition was reached under white light illumination.

A model will now be outlined for explaining the present results. According to the piezoelectric characteristics of CdS, mechanical bending of an (00.1) wafer about the [010] axis induces polarization $P_3$ in the [001] direction:

$$P_3 = \pm d_{31} \sigma_2, \qquad (1)$$

where $d_{31}$ (equal to $d_{32}$) is the piezoelectric constant and $\sigma_2$ is the induced stress in the [210] direction. The + sign in eq. (1) refers to the S (00.$\bar{1}$) surfaces and the − sign to the Cd (00.1) surfaces; $\sigma_2$ is related to the corresponding strain $\epsilon_2$ according to:

$$\sigma_2 = c^* \epsilon_2, \qquad (2)$$

where $c^*$ is the elastic stiffness; its value calculated for the present bending configuration is $5.6 \times 10^{10}$ N/m².

A macroscopic manifestation of the polarization in eq. (1) is not possible in the bulk since the carrier concentration is high ($n_b = 10^{16}$/cm³) and their redistribution shorts out the polarization. However, in the depleted surface region where the free carrier concentration is essentially zero, polarization $P_3$ can be readily manifested macroscopically. Assuming that, upon bending (at time $t=0$), the observed changes in cpd at $t=0^+$ are not shielded by the surface states and that a Schottky-type surface barrier is present, then it can be shown that the system at hand can be described by the following set of one-dimensional equations:

$$D_3 = P_3 + \epsilon \epsilon_0 E_3, \qquad (3)$$

$$\delta D_3/\delta x_3 = \rho, dE_3/dx_3 = -E_3, \qquad (4)$$

$$|\Delta D_3| \text{ surface} = Q_{ss}, \qquad (5)$$

where $D_3$ is electric displacement; $\epsilon$ is the dielectric constant; $\epsilon_o$ is the permitivity of free space; $E_3$ is the electric field; $\rho$ is the charge density; V is the potential barrier; $Q_{ss}$ is the surface state charge density.

For $V_s = V_x^0 + \Delta V_s << -kT/q$ (Schottky-type surface barrier), it follows from the above set of equations (for $t=0^+$):

$$|V_s^0 + \Delta V_s|^{1/2} = |V_s^0|^{1/2} \pm \alpha d_{31} \epsilon_{2s}, \qquad (6)$$

where $\alpha = c/(2qn_b \epsilon \epsilon_0)^{-1/2}$, $n_b$ is the free carrier concentration in the bulk and $\epsilon_{2s}$ is the strain at the surface. Introducing a measurable quantity Z defined as $Z = |d\Delta V_x/d\epsilon_{2s}|t=0^+$, there is obtained from eq. (6) the following expression:

$$Z^2 = 4\alpha^2 d_{31}^2 |V_s^0 + \Delta V_s| \qquad (7)$$

According to eq. (7), $Z^2$ is linearly related to $\Delta V_s$, i.e., the cpd upon bending ($t=0^+$). Experimental results bear out this relationship. It will be appreciated on the basis of the foregoing discussion that very small magnitudes of force can be sensed by employing the sensor herein disclosed.

An a-c displacement signal can also be generated if the wafer-reference electrode 5 capacitance is maintained in a constant (non-vibrating) configuration and the cpd is varied periodically, as is previously noted. The periodic variation in cpd can be produced by chopped incident light. The a-c signal properly (Fourier) analyzed can serve for determining (and continuously recording) a-c surface photovoltage. The sample-reference electrode configuration shown in FIG. 1 can be employed as can, also, the cpd-measuring circuit. The chopping is effected by the light chopper 4, as mentioned, which is provided with its own input reference signal. In one experiment, the light incident on the wafer 1 was maintained at $3 \times 10^{15}$ photons km². Observed surface states in the prismatic surfaces of CdS under atmospheric pressure and corresponding photostimulated transitions, are given in Table 1.

TABLE 1

OBSERVED SURFACE STATES IN THE PRISMATIC SURFACES OF CdS UNDER ATMOSPHERIC PRESSURE AND CORRESPONDING PHOTO-STIMULATED TRANSITIONS

| Energy position (eV) | Transitions corresponding to an increase in surface barrier height (quenching effect) | Transitions corresponding to a decrease in surface barrier height | Sum of transition energies (eV) |
|---|---|---|---|
| $E_c - E_t \cong 0.05$ | $\lambda_1 \cong 0.52$ to $0.53$ $\mu$m<br>$h_{\nu 1} \cong 2.4$ eV | not observed | |
| $E_c - E_t \cong 0.4$ | $\lambda_2 \cong 0.62$ $\mu$m<br>$h_{\nu 2} \cong 2.0$ eV | $\lambda_7 > 2.5$ $\mu$m<br>$h_{\nu 7} < 0.5$ eV | $< 2.5$ |
| $E_c - E_t \cong 0.8$ | $\lambda_3 \cong 0.79$ $\mu$m<br>$h_{\nu 3} \cong 1.57$ eV | $\lambda_6 \cong 1.58$ $\mu$m<br>$h_{\nu 6} \cong 0.78$ eV | $\sim 2.35$ |
| $E_c - E_t \cong 1.1$ | not observed | $\lambda_4 \cong 1.1$ $\mu$m<br>$h_{\nu 4} \cong 1.1$ eV | |
| $E_t - E_v \cong 0.83$ | $\lambda_5 \cong 1.5$ $\mu$m<br>$h_{\nu 5} \cong 0.83$ eV | | |

The surface states are shown schematically in FIG. 2.

From the above explanation it can be seen that the cpd varies as some function of intensity of incident light upon the wafer 1. It also varies as a function of the wavelength of the incident light. Thus, cpd can be employed to sense impinging radiation itself. Furthermore, if the wafer 1 is enclosed within a vacuum chamber, represented by the block designated 11 in FIG. 3, and subjected to a high vacuum ($\sim 10^{-11}$ torr), the cpd can be employed to sense very small magnitudes of a gas which may enter the chamber 11 through a controlled leak or through a gas inlet valve. The gas such as oxygen, for example, entering the chamber 11 is absorbed upon the surface of the wafer 1 and effects changes in the cpd. A most important use of the concepts herein disclosed is measurement of traces of a gas by means of noting changes of mechanical stress of the semiconductor wafer caused by the gas, an original bias stress being caused by light impinged upon a properly oriented, non-centrosymmetric semiconductor wafer. This latter concept is discussed in the next several paragraphs.

In FIG. 3 the semiconductor wafer is designated 1A. The wafer 1A is fastened rigidly at one end 12, as shown. The free end of the wafer 1A is, thus, free to vibrate. In this situation the thin CdS wafer 1A exhibits pronounced bending when illuminated with white light. Chopped white light can be employed to excite the wafer to its natural frequency. However, the amplitude of vibration has been found to be a function of the frequency of the incident radiation. Thus, the embodiment of FIG. 3 can be used to detect radiation frequency in and around the visible spectrum or the presence of gases when light of a known frequency is used. Some experimental work is discussed in the next several paragraphs, the wafer being made of CdS, GaAs or other such semiconductors in work discussed in connection with FIGS. 3 and 5. It should be preliminarily noted that two parameters can be measured to give a measurable indication of the thing to-be-sensed. First, the cpd can be sensed employing an arrangement similar to FIG. 1 and, second, mechanical vibration of the wafer can be sensed employing the weak light beam shown schematically at 17 and a pick-up mechanism 18; the latter can be merely a movie-type screen.

The wafers, employed in the arrangement depicted by FIG. 3, measured about $10 \times 3 \times 0.015$ mm. They were cut from carefully selected high-purity n-type CdS single crystals with a resistivity of about 1 $\Omega$cm. They were mechanically ground and then were chemically etched in 0.5N $k_2Cr_2O_7$: 16N $H_2SO_4$ to their final dimensions. They exhibited initial "spontaneous bending" consistent with previously noted results on wafers of III–V compounds. The illumination arrangement consisted of a xenon lamp, a double prism monochrometor and a variable frequency chopper. Typically, $10^{14}$ photon/sec. ($h\nu \simeq 2.5$ eV) were used to excite the wafers to their fundamental frequency vibration, which was of the order of 100 Hz. The resulting relative amplitude (amplitude divided by the length of the sample) of the vibration was of the order of $5 \times 10^2$. The amplitude was determined by means of a collimated laser beam 17 reflected from the CdS wafers upon the screen 18. The intensity of the cw laser beam ($\lambda = 0.63$ $\mu$m) was reduced to a level that did not affect the bending of the wafers under study. Background illumination had to be excluded. Surface photovoltage was also measured as the light-induced change in the contact potential difference by employing a gold reference electrode 5, as before.

The spectrum of the amplitude of vibration as a function of the wavelength of the incident radiation exhibited by the CdS wafers is very similar to their surface-photovoltage spectrum and differs considerably from their photoconductivity spectrum. Accordingly, it is concluded that the observed photomechanical effect is a surface effect associated with the light-induced changes in the electric field at the surface (surface barrier). In view of the piezoelectric properties of CdS, the electric field can be related to the resulting strain on the basis of the converse piezoelectric effect. Thus, to explain the observed photomechanical effect, a model is proposed involving (a) a surface-photovoltage step and (b) an electromechanical step. Step (a) has been discussed previously herein and analyzed for CdS surfaces. Regarding step (b) in a matrix notation the electric field $E_i$ in FIG. 5 is related to the strain components $\epsilon_j$ by $$\epsilon_j = d_{ij} E_i, \tag{8}$$

wherein $d_{ij}$ is piezoelectric coefficient. For the wurtzite structure the $(d_{ij})$ matrix is $$(d_{ij}) = \begin{pmatrix} . & . & . & . & d_{15} & . \\ . & . & . & d_{24} & . & . \\ d_{31} & d_{32} & d_{33} & . & . & . \end{pmatrix}, \tag{9}$$

where $d_{31} = d_{32}$ and $d_{15} = d_{24}$. Accordingly, an electric field $E = (0,0E_3)$ perpendicular to the basal planes (FIG. 5) induces strain $\epsilon = (\epsilon_1, \epsilon_2, \epsilon_3, 0,0,0)$ with components in the $x_1$, [100] and $x_2$, [120], directions as well as in the $x_3$, [001], direction. The electric field (and thus the strain components) in the basal surfaces of the wafer is in opposite directions since both surfaces have a depletion layer. Consequently, one surface is under compression and the other under tension and the wafer undergoes spontaneous bending (this bending is in addition to that caused by the elastic strain associated with the bonding configuration of the surfaces). Under illumination the electric field decreases in both surfaces leading to a decrease in the strain and, thus, in the extent of bending. The wafer is excited to its fundamental frequency vibration when the electric field is modulated at that characteristic frequency — in the present case by chopped light.

Since both strain components $\epsilon_1$ and $\epsilon_2$ are affected by illumination, it is expected that chopped light should stimulate two fundamental vibrations, i.e., that shown schematically in FIGS. 3 and a twisting vibration, not shown. Indeed, both these vibrations were experimentally observed with samples having their width dimension comparable to their length.

Further support for the proposed model was provided by the fact that the electromechanical step of the effect was found to be reversible, i.e., mechanical slight bending of the wafers (parallel to the $x_1$ or $x_2$ axis) induced a polarization along the $x_3$ which was manifested as a pronounced change of the contact-potential difference (of the order of 0.5 V) in both basal planes. Appreciable contributions to the photomechanical effect by thermoelastic, pyroelectric or light pressure effects are not likely, since sub-bandgap, low-intensity monochromatic radiation is involved and since the direction of bending is independent of the direction of the light propagation.

The photomechanical effect should be exhibited by all non-centrosymmetric semiconductors with the wurtzite structure and possibly by those with the zinc-blende structure. The presence of a strongly depleted layer at the surface enhances the magnitude of the effect. Rectifying junctions in these materials when perpendicular to the polar axis also lead to photomechanical effects.

Since the amplitudes of vibration spectra are similar to the surface-photovoltage spectra, they apparently provide a relatively simple means for determining the energy position of the surface states. Thus, a dip at $\lambda \simeq 0.52$ $\mu$m in the amplitude of vibration spectrum was found and is attributed to the excitation of electrons from the valence band to shallow surface states with an energy position $\simeq 0.05$ eV below the conduction band, just as in the case of the surface-photovoltage spectrum. Change in the fundamental frequency of vibration resulting from changes in the ambient should make possible the study of the mechanical properties of surfaces.

The sensitivity of the amplitude of vibrations to incident radiation (under the present experimental conditions, $10^{12}$ photons/cm$^2$ sec. could readily be detected) shows that the photomechanical effect can be employed for the design of a new type of a sensitive light sensing device of the type above noted, based on either the modulation of the surface barrier or the barrier of an appropriately located rectifying junction. This effect can also serve as the basis for the photogeneration of mechanical waves (e.g., ultrasonic phonons) by modulating the lattice strain in single crystals or, conversely, as a phonon detector.

It should be further pointed out that when ambient molecules introduce surface states through absorption the amplitude of vibration of a wafer like the wafer 1A is very sensitive to even trace amounts of these molecules at the energy of illumination corresponding to the energy of the introduced surface states. Accordingly, the photomechanical effect serves as the basis for extremely sensitive detectors of gaseous (or liquid) species. By employing a variety of non-centrosymmetric semiconductors it is possible to encompass a number of molecular species which, through absorption, introduce distinct surface states.

It will be appreciated that the invention herein disclosed is multi-faceted. Accordingly, brief summary remarks are believed in order and are contained in this paragraph. The system disclosed can be employed to measure a force exerted upon the semiconductor crystal. This effect is sensed by noting changes in the cpd effected by the force and by changes in the cpd as a consequence of changes in the force. Thus, the system is capable of sensing steady or periodic mechanical forces. The system is also capable of sensing the presence of light and/or the frequency of such light, again by noting changes in the cpd or, as above noted, in the case of non-centrosymmetric crystals, by noting mechanical vibrational effects upon the crystal wrought by the radiation. The system is capable of sensing the presence of particular gases, again by the changes in cpd effected by such gases.

Modification of the invention herein disclosed will occur to persons skilled in the art, and all such modifications are deemed to be within the spirit and scope of the invention as defined in the appended claims.

What is claimed is:

1. A gas sensor comprising:
    a. a semiconductor wafer formed of a non-centrosymmetric material having a high energy gap and selected from the group consisting of materials having wurtzite and zinc-blende structure;
    b. a vacuum chamber containing the wafer and adapted to receive traces of a gas that introduces surface states in the wafer through absorption;
    c. a source of illumination whose energy corresponds to the energy of the introduced surface states, said source illuminating the wafer for causing the latter to deflect an amount dependent on the wavelength of the illumination; and
    d. means for measuring the deflection of the wafer for detecting the presence of said gas in the chamber.

2. A sensor according to claim 1 wherein said source produces monochromatic illumination of said wafer.

3. A sensor according to claim 2 wherein said source produces chopped monochromatic illumination of said wafer for causing the latter to vibrate at a frequency dependent on the chopping frequency and with an amplitude dependent on the wavelength of the illumination.

4. A sensor according to claim 3 wherein said source includes a xenon lamp producing a beam, a monochromator responsive to said beam to produce an excitation beam incident on the wafer, and a light chopper for periodically chopping said excitation beam.

5. A sensor according to claim 4 wherein the means for measuring the deflection of said wafer includes a light beam incident on the wafer and reflected thereby onto a screen whereby the amplitude of vibration of said wafer can be measured.

6. A sensor according to claim 1 wherein said source produces steady state monochromatic illumination of said wafer.

7. A sensor according to claim 6 wherein said means for measuring the deflection of said wafer includes a vibrating probe for detecting the contact potential difference that arises due to changes in surface states in response to illumination of said wafer.

8. A sensor according to claim 1 wherein the material of the wafer has a structure like zinc-blende.

9. A sensor according to claim 4 wherein the material of the wafer has a structure like wurtzite.

10. A sensor according to claim 1 wherein the gas is oxygen and the wafer material is cadmium sulfide.

11. A method for detecting traces of oxygen in a vacuum chamber comprising the steps of:
 a. placing a cadmium sulfide wafer in the vacuum chamber;
 b. illuminating the wafer with radiation whose energy corresponds to the energy of surface states introduced by oxygen for causing the wafer to deflect an amount dependent on the wavelength of the illumination; and
 c. measuring the deflection of the wafer when it is known that oxygen is absent from the chamber so that changes in the deflection due to the presence of oxygen can be detected.

* * * * *